United States Patent
Negishi et al.

(10) Patent No.: US 7,923,224 B2
(45) Date of Patent: Apr. 12, 2011

(54) METHOD OF RECOVERING LIPASE ACTIVITY

(75) Inventors: Satoshi Negishi, Yokosuka (JP); Junko Suzuki, Yokosuka (JP); Yoshie Yamauchi, Yokosuka (JP)

(73) Assignee: The Nisshin OilliO Group, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 12/266,617

(22) Filed: Nov. 7, 2008

(65) Prior Publication Data

US 2009/0075349 A1    Mar. 19, 2009

Related U.S. Application Data

(63) Continuation of application No. PCT/JP2007/059751, filed on May 11, 2007.

(30) Foreign Application Priority Data

May 11, 2006    (JP) .................... 2006-132639

(51) Int. Cl.
C12P 7/64 (2006.01)
C12N 9/98 (2006.01)
C12N 11/14 (2006.01)

(52) U.S. Cl. .................. 435/134; 435/176; 435/187
(58) Field of Classification Search .................. None
See application file for complete search history.

(56) References Cited

U.S. PATENT DOCUMENTS

| | | | |
|---|---|---|---|
| 4,818,695 A | | 4/1989 | Eigtved |
| 5,342,768 A | * | 8/1994 | Pedersen et al. ............. 435/134 |
| 5,480,787 A | | 1/1996 | Negishi et al. |
| 5,902,738 A | * | 5/1999 | Orsat et al. .................... 435/155 |
| 6,156,548 A | * | 12/2000 | Christensen et al. .......... 435/134 |
| 6,372,472 B1 | * | 4/2002 | Nehls et al. .................... 435/198 |

FOREIGN PATENT DOCUMENTS

| | | | |
|---|---|---|---|
| JP | 60-98984 A | | 6/1985 |
| JP | 61-202688 A | | 9/1986 |
| JP | 1-262795 A | | 10/1989 |
| JP | 2-138986 A | | 5/1990 |
| JP | 3-61485 A | | 3/1991 |
| JP | 5-137574 A | | 6/1993 |
| JP | 7-79789 A | | 3/1995 |
| JP | 2668187 B2 | | 10/1997 |
| JP | 2000-106873 A | | 4/2000 |
| JP | 2001-178488 | * | 3/2001 |
| WO | WO 00/56869 A | | 9/2000 |

OTHER PUBLICATIONS

Kiens et al. (1998) Am. J. Physiol. Endocrin. Metab. 275; 332-337.*
Vainio et al. (1983) J. Biol. Chem. 258(9): 5477-82.*
Negishi Satoshi et al.: "Activation of Powered Lipase by Cluster Water and the Use of Lipase Powders for Commercial Esterification of Food Oils," Enzyme and Microbial Technology, Stoneham, MA, US, vol. 32, No. 1, Jan. 2, 2003, pp. 66-70, XP002456965, ISSN: 0141-0229.
Supplementary European Search Report for European Patent Application No. EP 07743186 dated Sep. 14, 2009.
PCT/ISA/210, (Jun. 5, 2007).
PCT/ISA/237, (May 25, 2007).

* cited by examiner

Primary Examiner — Lisa J Hobbs
(74) Attorney, Agent, or Firm — Buchanan Ingersoll & Rooney PC

(57) ABSTRACT

The present invention discloses a method of recovering lipase activity which comprises the steps of using a lipase derived from *Thermomyces* sp. and immobilized on a carrier, or a lipase powder composition which comprises a filter aid and the lipase derived from *Thermomyces* sp. and immobilized on a carrier which is crushed into the average particle size of 1 μm or larger and smaller than 300 μm in an esterification or transesterification reaction; and washing said lipase or lipase powder composition with triacylglycerol. According to this method, the decreased lipase activity can be effectively recovered.

9 Claims, 2 Drawing Sheets the field of the invention

METHOD OF RECOVERING LIPASE ACTIVITY

TECHNICAL FIELD OF THE INVENTION

The present invention relates to methods of recovering lipase activity such as various esterifying or transesterifying abilities of a specific immobilized lipase or lipase powder composition. The present invention also relates to esterification reactions or transesterification methods of oils and fats wherein a recovered immobilized lipase or lipase powder composition is used.

BACKGROUND OF THE INVENTION

Lipase is widely used in the esterification reaction between various carboxylic acids such as fatty acids and alcohols such as monoalcohols and polyalcohols; or the transesterification reaction between multiple carboxylic esters. Among them, a transesterification reaction is an important technology to modify animal and vegetable fats and oils, and to produce esters of various fatty acids, sugar esters and steroid. When lipase which is a hydrolase of fats and oils is used as a catalyst of these reactions, the transesterification reaction can be conducted under the mild condition of room temperature to around 70° C. Thus, as compared with conventional chemical reactions, lipase not only inhibits side reactions and decreases energy costs, but also has high safety since lipase as a catalyst is a natural product. Further, objective compounds can be effectively produced because of the substrate specificity and place specificity thereof. However, though lipase powder is directly used in a transesterification reaction, the activity of lipase does not generally sufficiently express. In addition, it is difficult to uniformly disperse lipase which is basically soluble in water to an oil-based raw material, and also difficult to collect it. Accordingly, it is common that lipase is immobilized on a certain carrier such as an anion-exchange resin (Patent Literature 1), a phenol adsorption resin (Patent Literature 2), a hydrophobic carrier (Patent Literature 3), a cation-exchange resin (Patent Literature 4) and a chelate resin (Patent Literature 5), and used in an esterification or transesterification reaction.

However, since the lipase activity decreases when lipase is immobilized on a carrier, various technologies have been developed using lipase powder.

More specifically, the method is proposed which comprises the steps of dispersing lipase powder in a raw material containing an ester(s) in the presence or absence of an inactive organic solvent so that 90% or more of the particle size of the dispersed lipase powder particles is kept within 1 to 100 μm in the transesterification reaction; and then conducting the transesterification reaction (Patent Literature 6). Further, it is also proposed to use enzymatic powder which is obtained by drying an enzymatic solution containing a phospholipid(s) and lipid-soluble vitamin(s) (Patent Literature 7).

Meanwhile, since lipase which is an enzyme is expensive, it is collected after the completion of the reaction and repeatedly used, and it is first discarded when the lipase activity considerably decreases. However, if the decreased lipase activity can be recovered, usability of lipase would dramatically improve. Thus, from the industrial viewpoint, the effective method of recovering lipase activity has been desired to be developed.

Patent Literature 1: JP-A 60-98984
Patent Literature 2: JP-A 61-202688
Patent Literature 3: JP-A 2-138986
Patent Literature 4: JP-A 3-61485
Patent Literature 5: JP-A 1-262795
Patent Literature 6: JP-B 2668187
Patent Literature 7: JP-A 2000-106873

DISCLOSURE OF THE INVENTION

The object of the present invention is to provide methods of being able to recover decreased lipase activity.

The further object of the present invention is to provide esterification methods or transesterification methods each of which comprises the step of using an immobilized lipase or lipase powder composition each of which has the recovered lipase activity.

The present invention has been completed based on the finding that, on a specific immobilized lipase or lipase powder composition which combines a crushed product of the specific immobilized lipase with a filter aid, when washing said lipase or lipase powder composition of which lipase activity has decreased with triacylglycerol, the original lipase activity thereof can be recovered.

Namely, the present invention provides a method of recovering lipase activity which comprises the steps of using a lipase derived from *Thermomyces* sp. and immobilized on a carrier, or a lipase powder composition which comprises a filter aid and the lipase derived from *Thermomyces* sp. and immobilized on a carrier which is crushed into an average particle size of 1 μm or larger and smaller than 300 μm in an esterification or transesterification reaction; and washing said lipase or lipase powder composition with triacylglycerol.

The present invention also provides an esterification or transesterification reaction which comprises the steps of using a lipase derived from *Thermomyces* sp. and immobilized on a carrier, or a lipase powder composition which comprises a filter aid and the lipase derived from *Thermomyces* sp. and immobilized on a carrier which is crushed into an average particle size of 1 μm or larger and smaller than 300 μm in an esterification or transesterification reaction; separating the lipase or lipase powder composition from the reaction system, and washing it with triacylglycerol to recover the lipase activity thereof; and then, conducting an esterification or transesterification reaction using the resulting immobilized lipase or lipase powder composition.

BEST MODE FOR CARRYING OUT THE INVENTION

Figure 1:
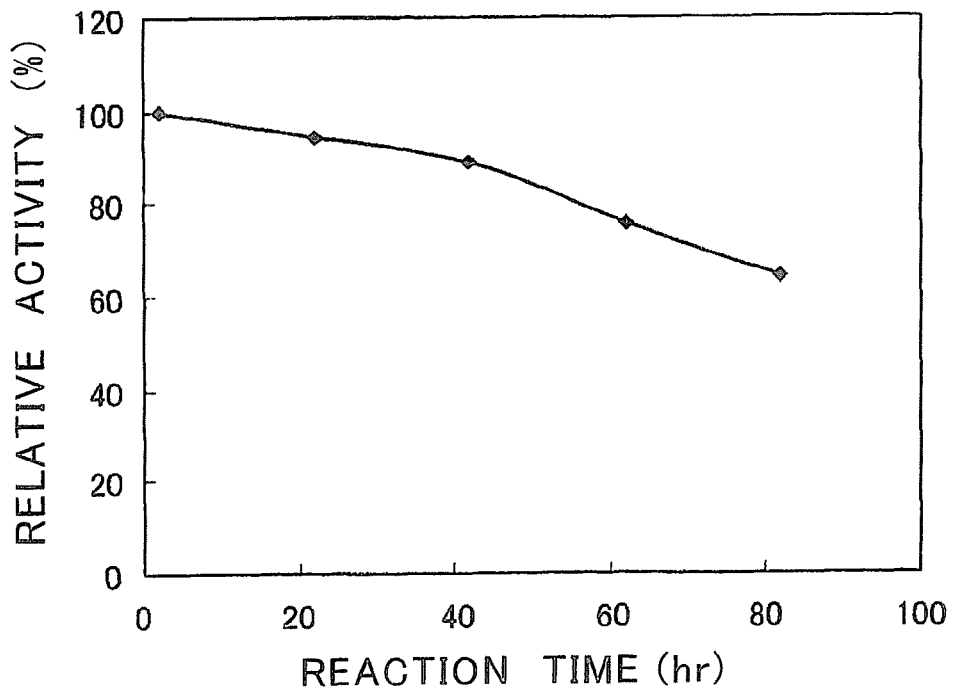
FIG. 1 shows the decrease of the transesterification activity over time when a lipase powder composition is used in the transesterification reaction (Example 1(3)).

Lipase used in the present invention is derived from *Thermomyces* sp. and immobilized on a carrier, preferably a silica carrier. In the present invention, it is possible to use said lipase directly or to use said lipase which is crushed into the average particle size of 1 μm or larger and smaller than 300 μm. More specifically, it is preferable that the average particle size of said lipase immobilized on a silica carrier is around 300 to 1000 μm. Such an immobilized lipase can be obtained, for example, as Lipozyme TL-IM produced by Novozymes A/S.

When crushing such an immobilized lipase, it is preferable to use a normal mill and crush it into the average particle size of 1 μm or larger and smaller than 300 μm, preferably 1 to 200 μm, more preferably 1 to 100 μm, and particularly preferably 20 to 100 μm. Examples of the mill include a mortar, a Rod mill, a cutter mill, a millstone (Mycolloider, Masscolloider), a coffee mill, a power mill, a pin mill, an impact mill (a hammer mill, a ball mill), a roller mill, a current mill, a homogenizer, and an ultrasonic mill.

When lipase intended in the present invention is the above crushed product, it is preferable to use it in combination with a filter aid. Examples of the filter aid include inorganic filter aids such as celite and organic filter aids such as fibers, e.g. cellulose and crushed products thereof. Among them, organic filter aids, especially organic polymer filter aids are preferable, and cellulose and the like are particularly preferable. Preferable examples thereof include trade name: KC Flock produced by Nippon Paper Chemicals Co., Ltd. It is preferable that a filter aid is also powdery and has 10 to 90 μm in the average particle size.

The mass ratio of the above crushed lipase product to a filter aid is preferably 1/10 to 10/1, and particularly preferably 1/7 to 2/1.

Though the above immobilized lipase or lipase powder composition used in the present invention can be directly used in an esterification or transesterification reaction of oils and fats, they can be purified by contacting them with a long-chain fatty acid triglyceride and a medium-chain fatty acid triglyceride; and then collecting them. At the same time, it is possible to improve the lipase activity thereof.

As a long-chain fatty acid triglyceride and a medium-chain fatty acid triglyceride herein used, it is preferable to use those mentioned in the following section on washing of an immobilized lipase or lipase powder composition.

It is preferable to use a long-chain fatty acid triglyceride and a medium-chain fatty acid triglyceride in the mass ratio of 95:5 to 50:50, and it is preferable to contact 2 to 100-fold mass of triglyceride per a total mass of a lipase.

The esterification reaction using the immobilized lipase or lipase powder composition is preferably the method comprising the steps of esterifying fats and oils in the presence of the immobilized lipase or lipase powder composition; then, collecting the immobilized lipase or lipase powder composition and recycling them.

Especially, since the lipase activity and usability in an esterification or transesterification reaction of the above lipase powder composition are improved enough to be recycled and used in these reactions, it is possible to suitably use the composition in modification of fats and oils by the transesterification of fats and oils on an industrial scale.

However, when repeatedly recycling and using such a lipase powder composition or immobilized lipase in an esterification or transesterification reaction, the lipase activity thereof such as esterifying or transesterifying abilities decreases corresponding to the number of use.

The present invention makes it possible that when such an immobilized lipase or lipase powder composition each of which lipase activity decreased is washed in a specific condition, the lipase activity thereof is improved and, on the lipase powder composition, the improved lipase activity and usability are sustained for a long period.

In the present invention, the immobilized lipase or lipase powder composition each of which lipase activity decreased can include those wherein the original lipase activity even slightly decreased. However, in terms of the industrial aspect, it is preferable to target those wherein the original lipase activity (100%) decreased to 70 to 50%.

Meanwhile, it is preferable that triacylglycerol used for washing an immobilized lipase or lipase powder composition is liquid at room temperature. It is particularly preferable to use a mixture of a long-chain fatty acid triglyceride and a medium-chain fatty acid triglyceride, each of which is used for purifying the lipase powder composition.

As the long-chain fatty acid triglyceride herein used, triglyceride of which a constituent fatty acid has 14 to 24 carbon atoms is preferable, and it is particularly preferably a vegetable oil selected from the group consisting of canola oil, soybean oil, sunflower oil, safflower oil and corn oil.

As the medium-chain fatty acid triglyceride, triglyceride of which a constituent fatty acid has 6 to 12 carbon atoms is preferable. It is possible to produce such a fatty acid triglyceride by a publicly known method or to use a marketed product thereof. Examples of the marketed product include trade name: ODO produced by The Nisshin OilliO Group, Ltd.

It is preferable to use a long-chain fatty acid triglyceride and a medium-chain fatty acid triglyceride in the mass ratio of 95:5 to 50:50, and it is preferable to contact 2 to 100-fold mass, and more preferably 5 to 50-fold mass of triglyceride per a total mass of a lipase.

Particularly, triacylglycerol used for washing is preferably raw oil for the transesterification.

It is preferable that an immobilized lipase or lipase powder composition is washed so that the above lipase or a lipase in the above lipase composition can sufficiently contact with above triacylglycerol. More specifically, washing is preferably conducted by stirring and dispersing an immobilized lipase or lipase powder composition used in an esterification or transesterification reaction in triacylglycerol; and separating them from triacylglycerol.

The contact, more specifically stirring is preferably conducted at 10 to 45° C. and particularly preferably at room temperature; and preferably for 2 hours or more, more preferably for 10 hours or more, and particularly preferably for 12 to 48 hours. If desired, it may be conducted for 48 hours or more.

The agitator used for stirring is not particularly limited, and it is preferable to use a propeller mixer, a magnetic stirrer, Threeone motor, or the like.

Thus, an immobilized lipase or a lipase in a lipase powder composition is sufficiently contacted with triacylglycerol; filtered in accordance with the ordinary method to separate the immobilized lipase or lipase powder composition from triacylglycerol; and then used again in an esterification or transesterification reaction.

Until now, a lipase of which lipase activity decreased due to the use thereof in various reactions has been discarded. However, according to the method of the present invention, since the lipase activity can be recovered, the use duration of a lipase can be extended and the cost of the products which are produced using the lipase can be decreased. Thus, the present invention has many advantages from the industrial viewpoint.

Next, Examples will further illustrate the present invention.

EXAMPLE 1

(1) 1 kg of Lipozyme TL-IM of Novozymes A/S having the average particle size of 800 μm in was crushed with a pin mill (Fine impact mill 100 UPZ) of Hosokawa Micron Corporation at 17600 rpm. The particle size of the crushed lipase was measured with a particle size distribution analyzer LA-500 of HORIBA, Ltd, and the average particle size thereof was 13.8 μm. 1 kg of cellulose powder of Nippon Paper Chemicals Co., Ltd. having the average particle size of 30 μm was added as a filter aid to the lipase powder to prepare a lipase powder composition.

(2) 90 g of bleached canola oil and 10 g of ODO (a medium-chain fatty acid triglyceride) of The Nisshin OilliO Group, Ltd. were added to 5 g of thus obtained lipase composition, and stirred for 24 hours at room temperature. Then, the mixture was filtered to collect the lipase composition. Then, the transesterifying activity of this lipase composition was measured by the following method, and the relative activity thereof was 714 when defining the activity of Lipozyme TL-IM before crushing as 100.

Measurement Method of Lipase Activity

The lipase composition was added to the oil in which triolein and tricaprylin are mixed in 1:1 (w) and reacted at 60° C. 10 μL thereof was taken as a sample over time, diluted with 15 mL of hexane, and then, a solution wherein the lipase composition was filtered was taken as a sample for gas chromatography (GC). The solution was analyzed by GC (column: DB-1ht) and the reaction rate was calculated from the following formula. The GC conditions are: column temperature: beginning 150° C., temperature rising: 15° C./min., and final 370° C.

Reaction rate(%)={C34area/(C24area+C34area)}×100 wherein, C24 is tricaprylin; C34 is tricaprylin wherein one fatty acid is replaced by an oleic acid; and area is each area thereof. Based on the reaction rate of each time, the reaction rate constant k was calculated by an analysis software (origin ver. 6.1).

The lipase activity was represented by the relative activity when defining value k of Lipozyme TL-IM as 100.

(3) 1 weight % of the lipase composition obtained in above (2) was added to 85 g of bleached canola oil of The Nisshin OilliO Group, Ltd. and 15 g of ODO of The Nisshin OilliO Group, Ltd., and stirred for 19 hours at 60° C. to conduct a transesterification reaction. The transesterification rate was calculated over time, and the progression of the reaction was confirmed. As for the transesterification reaction, the glyceride composition was analyzed using gas chromatography, and the ratio of the transesterification reactant in a measured sample was calculated.

After the reaction, the lipase composition was filtered and collected, and the collected lipase composition was repeatedly used in the transesterification reaction. The reaction was further conducted several times. The change of the reaction rate represented by the relative rate is shown in FIG. 1.

From the results of FIG. 1, it was clarified that, when a total reaction time reaches about 82 hours, the lipase activity of the lipase composition decreases to about 60%.

(4) In above (3), the lipase composition of which relative activity decreased to about 60% was filtered and collected. Thus collected lipase composition was added to 18 g of bleached canola oil of The Nisshin OilliO Group, Ltd. and 2 g of ODO of The Nisshin OilliO Group, Ltd., and stirred for 24 hours at room temperature with a magnetic stirrer. After the lipase composition was collected by filtration, the transesterification was repeatedly conducted as mentioned in above (3). The change of the reaction rate represented by the relative rate is shown in FIG. 2.

Figure 2:
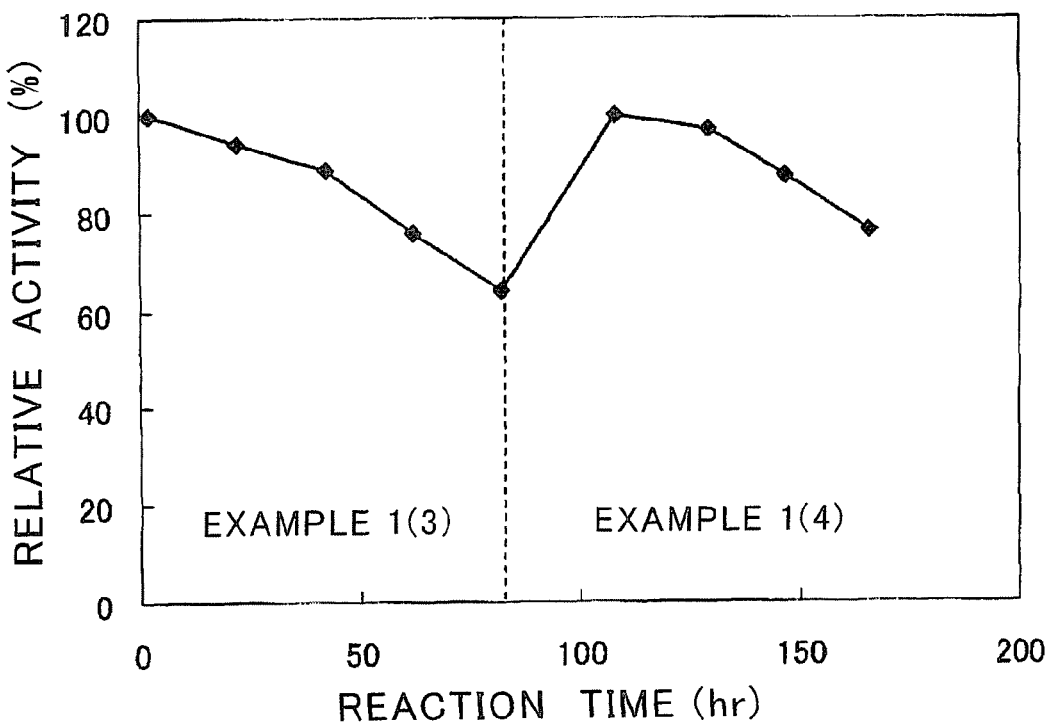
FIG. 2 shows that the transesterification activity is recovered by washing the lipase powder composition of which transesterification activity decreased in accordance with the present invention (Example 1(4)).

From the results of FIG. 2, it was clarified that the lipase activity is recovered by the original activity of 100% by washing with stirring the lipase composition of which activity decreased and that such lipase composition can be recycled and used a number of times.

EXAMPLE 2

(2-1) 90 g of bleached canola oil and 10 g of ODO of The Nisshin OilliO Group, Ltd. were added to 5 g of the lipase composition obtained in (1) of Example 1, and stirred for 2 hours at 60° C. Then, the mixture was filtered to collect the lipase composition. The transesterification activity of this lipase composition was measured by the same method as that of Example 1, and the relative activity thereof was 557.

(2-2) 1.2 weight % of the lipase composition obtained in above (2-1) was added to 100 g of soybean oil and 25 g of fully hydrogenated soybean oil of Yokozeki Fat & Oil Corporation, and stirred for 120 hours at 70° C. Then, the lipase composition was collected by filtration. The lipase activity of a part of the collected lipase composition was measured in the same method as that of Example 1 (2-2a). The previously collected lipase composition was dispersed in acetone and filtered. The filter cake thereof was collected again and dispersed in 50 g of mixed oil of bleached canola oil:ODO of The Nisshin OilliO Group, Ltd.=9:1 (w). Then, the mixture was filtered at room temperature to wash and substitute it, and the lipase composition was collected. The transesterification activity of this lipase composition was measured by the same method as that of Example 1 (2-2b). Each obtained activity was shown as the relative value in Table 1.

TABLE 1

| | Relative transesterification activity per a mass of a lipase preparation |
|---|---|
| Before crushing (TL-IM) | 100 |
| (2-1) | 557 |
| (2-2a) | 11 |
| (2-2b) | 200 |

EXAMPLE 3

5 weight % of Lipozyme TL-IM (immobilized lipase) of Novozymes A/S was added to 85 g of bleached canola oil of The Nisshim OilliO Group, Ltd. and 15 g of ODO of The Nisshin OilliO Group, Ltd., and stirred for 19 hours at 60° C. to conduct a transesterification reaction. The transesterification rate was calculated over time, and the progression of the reaction was confirmed. As for the transesterification reaction, the glyceride composition was analyzed using gas chromatography, and the ratio of the transesterification reactant in a measured sample was calculated.

Figure 3:
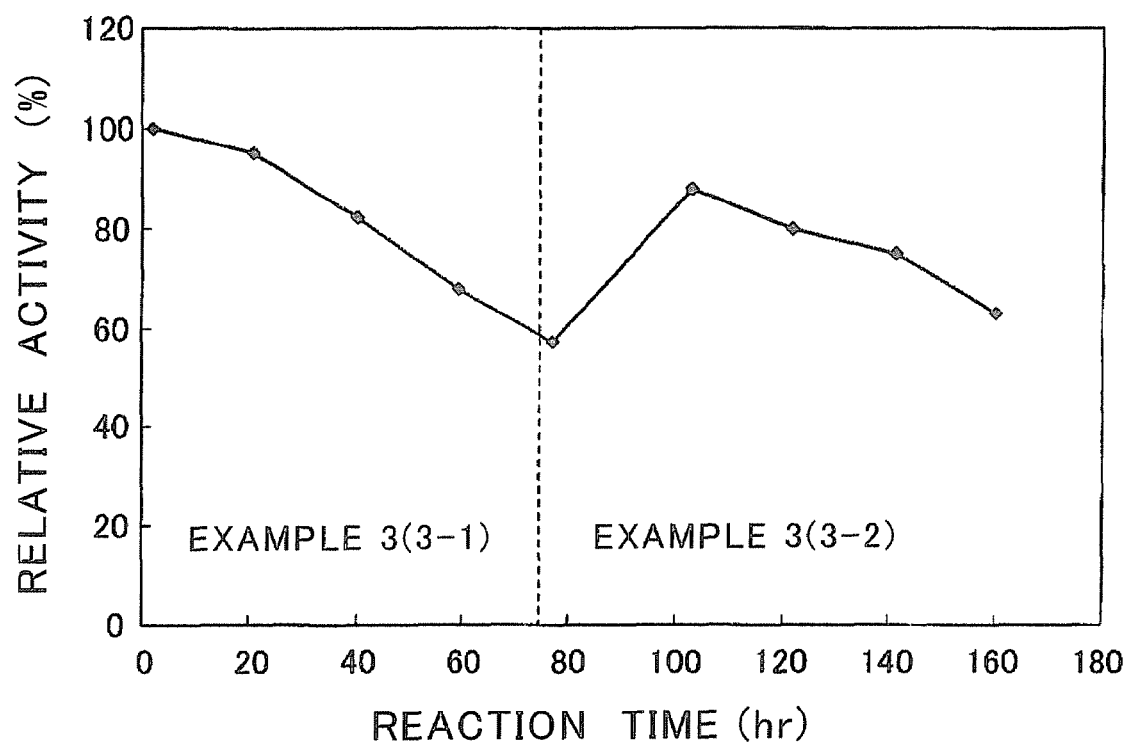
FIG. 3 shows that the transesterification activity is recovered by washing the immobilized lipase of which transesterification activity decreased in accordance with the present invention (Example 3(3-2)).

After the reaction, the above immobilized lipase was filtered and collected, and the collected immobilized lipase was repeatedly used in the transesterification reaction. The reaction was further conducted several times. The change of the reaction rate represented by the relative rate is shown in FIG. 3 (3-1).

The above immobilized lipase of which relative activity decreased to about 60% was filtered and collected. Thus collected immobilized lipase was added to 18 g of bleached canola oil of The Nisshin OilliO Group, Ltd. and 2 g of ODO of The Nisshin OilliO Group, Ltd., and stirred for 24 hours at room temperature. After the immobilized lipase was collected by filtration, the transesterification was repeatedly conducted as mentioned in above (3-1). The temporal change of the reaction rate represented by the relative rate is shown in FIG. 3 (3-2).

What is claimed is:

1. A method of recovering lipase activity which comprises the steps of using a lipase derived from *Thermomyces* sp. and immobilized on a carrier, or a lipase powder composition which comprises a filter aid and the lipase derived from *Thermomyces* sp. and immobilized on a carrier which is crushed into an average particle size of 1 μm or larger and smaller than 300 μm in an esterification or transesterification reaction; and
   washing said lipase or lipase powder composition with triacylglycerol,
   wherein the triacylglycerol comprises at least one medium-chain fatty acid triglyceride.

2. The method according to claim 1, wherein the triacylglycerol is liquid at a room temperature.

3. The method according to claim 1, wherein the triacylglycerol is raw oil for the transesterification.

4. The method according to claim 1, wherein the washing is conducted by the steps of stirring and dispersing the immobilized lipase or the lipase powder composition used in the esterification or transesterification reaction in triacylglycerol; and separating the lipase or the lipase powder composition from triacylglycerol.

5. The method according to claim 1, wherein the carrier is silica.

6. The method according to claim 1, wherein the average particle size of the crushed product is 1 to 200 μm.

7. The method according to claim 1, wherein the filter aid is cellulose.

8. The method according to claim 1, wherein the filter aid is powdery and the average particle size thereof is 10 to 90 μm.

9. A method of an esterification or transesterification reaction which comprises the steps of using a lipase derived from *Thermomyces* sp. and immobilized on a carrier, or a lipase powder composition which comprises a filter aid and the lipase derived from *Thermomyces* sp. and immobilized on a carrier which is crushed into an average particle size of 1 μm or larger and smaller than 300 μm in an esterification or transesterification reaction; separating the lipase or lipase powder composition from the reaction system, and washing the lipase or lipase powder with triacylglycerol to recover the lipase activity thereof; and then, conducting an esterification or transesterification reaction using the resulting immobilized lipase or lipase powder composition.

* * * * *